(12) United States Patent
Piper

(10) Patent No.: US 8,693,744 B2
(45) Date of Patent: Apr. 8, 2014

(54) SYSTEMS AND METHODS FOR GENERATING A CONTOUR FOR A MEDICAL IMAGE

(75) Inventor: Jonathan William Piper, Cleveland Hts, OH (US)

(73) Assignee: MIM Software, Inc., Cleveland, OH (US)

( * ) Notice: Subject to any disclaimer, the term of this patent is extended or adjusted under 35 U.S.C. 154(b) by 950 days.

(21) Appl. No.: 12/772,383

(22) Filed: May 3, 2010

(65) Prior Publication Data

US 2011/0271215 A1    Nov. 3, 2011

(51) Int. Cl.
*G06K 9/00*    (2006.01)
*G06K 9/34*    (2006.01)

(52) U.S. Cl.
USPC .......................................... 382/128; 382/173

(58) Field of Classification Search
USPC ........................ 382/128, 173, 284; 345/631
See application file for complete search history.

(56) References Cited

U.S. PATENT DOCUMENTS

| | | | |
|---|---|---|---|
| 5,365,599 A * | 11/1994 | Seto et al. | 382/242 |
| 6,031,935 A | 2/2000 | Kimmel | |
| 6,396,939 B1 | 5/2002 | Hu et al. | |
| 6,445,819 B1 * | 9/2002 | Kinjo | 382/173 |
| 7,158,692 B2 | 1/2007 | Chalana et al. | |
| 2005/0084178 A1 | 4/2005 | Lure et al. | |
| 2007/0116334 A1 | 5/2007 | Fidrich et al. | |
| 2007/0116335 A1 | 5/2007 | Capolunghi et al. | |
| 2008/0009707 A1 | 1/2008 | Theriault | |
| 2009/0080731 A1 * | 3/2009 | Krishnapuram et al. | 382/128 |
| 2009/0080738 A1 | 3/2009 | Zur et al. | |
| 2009/0190809 A1 | 7/2009 | Han et al. | |
| 2009/0252395 A1 | 10/2009 | Chan et al. | |
| 2010/0045663 A1 * | 2/2010 | Chen et al. | 345/419 |
| 2010/0053208 A1 | 3/2010 | Menningen et al. | |
| 2011/0103654 A1 * | 5/2011 | Lavoie et al. | 382/128 |

OTHER PUBLICATIONS

Koompairojn, Soontharee, Semi-Automatic Segmentation and Volume Determination of Bran Mass-Like Lesion, 21st IEEE International Symposium on Computer-Based Medical Systems, 2008.

* cited by examiner

*Primary Examiner* — Yubin Hung
(74) *Attorney, Agent, or Firm* — Hahn Loeser & Parks LLP

(57) ABSTRACT

In accordance with the teachings described herein, systems and methods are provided for generating a contour for a medical image. The system may include a contour synthesis engine that is configured to receive a plurality of contours for a medical image, the plurality of contours identifying at least one object within the medical image. The contour synthesis engine may be further configured to synthesize a combined contour from the plurality of contours by selecting portions of the plurality of contours based on one or more pre-defined contour combination criterion, the one or more pre-defined contour combination criterion including a designated number of contour overlaps such that any region where at least the designated number of contours are overlapping is included in the combined contour. The system may also include a graphical user interface configured to display an overlay of the plurality of contours and the combined contour on the medical image, and to receive user input to modify the combined contour by adding an additional region from the plurality of contours.

25 Claims, 12 Drawing Sheets

SYSTEMS AND METHODS FOR GENERATING A CONTOUR FOR A MEDICAL IMAGE

FIELD

The technology described in this patent document relates generally to the field of contouring medical images.

BACKGROUND AND SUMMARY

Contouring is the process of identifying an object within an image by outlining or otherwise distinguishing the object from the rest of the image. Medical images, such as CT (computed tomography), MR (magnetic resonance), US (ultrasound), or PET (positron emission tomography) scans, are regularly contoured to identify certain pieces of anatomy within the image. For example, a radiologist or oncologist may contour a medical image to identify a tumor within the image. Software tools are available to assist in this type of "manual" contouring, in which the physician uses the software to create the contour by tracing the boundary of the object or objects within the image. In addition to manual contouring software, so-called automatic and semi-automatic contouring software products are also available. Automatic contouring software may be used to automatically detect an object or objects within an image and to automatically create a contour to identify the object(s) within the image. However, fully automated contouring software is not yet reliable for most medical imaging applications. Accordingly, semi-automatic contouring software is often used that automatically generates contours for an image based on at least some manually-created input, such as a previously contoured image of the same or similar anatomy.

In accordance with the teachings described herein, systems and methods are provided for generating a contour for a medical image. The system may include a contour synthesis engine that is configured to receive a plurality of contours for a medical image, the plurality of contours identifying at least one object within the medical image. The contour synthesis engine may be further configured to synthesize a combined contour from the plurality of contours by selecting portions of the plurality of contours based on one or more pre-defined contour combination criterion, the one or more pre-defined contour combination criterion including a designated number of contour overlaps such that any region where at least the designated number of contours are overlapping is included in the combined contour.

A processor-implemented method of generating a contour for a medical image may include the steps of receiving a plurality of contours that identify an object within the medical image, and synthesizing a combined contour from the plurality of contours by selecting portions of the plurality of contours based on one or more pre-defined contour combination criterion. In certain embodiments, the one or more pre-defined contour combination criterion may comprise a pre-defined number of overlapping contours such that any portion of the plurality of contours that includes at least the pre-defined number of overlapping contours is included in the combined contour. In addition, some embodiments may include the step of receiving a user input to modify the combined contour by adding an additional region or removing a region from the plurality of contours.

DETAILED DESCRIPTION

Figure 1:
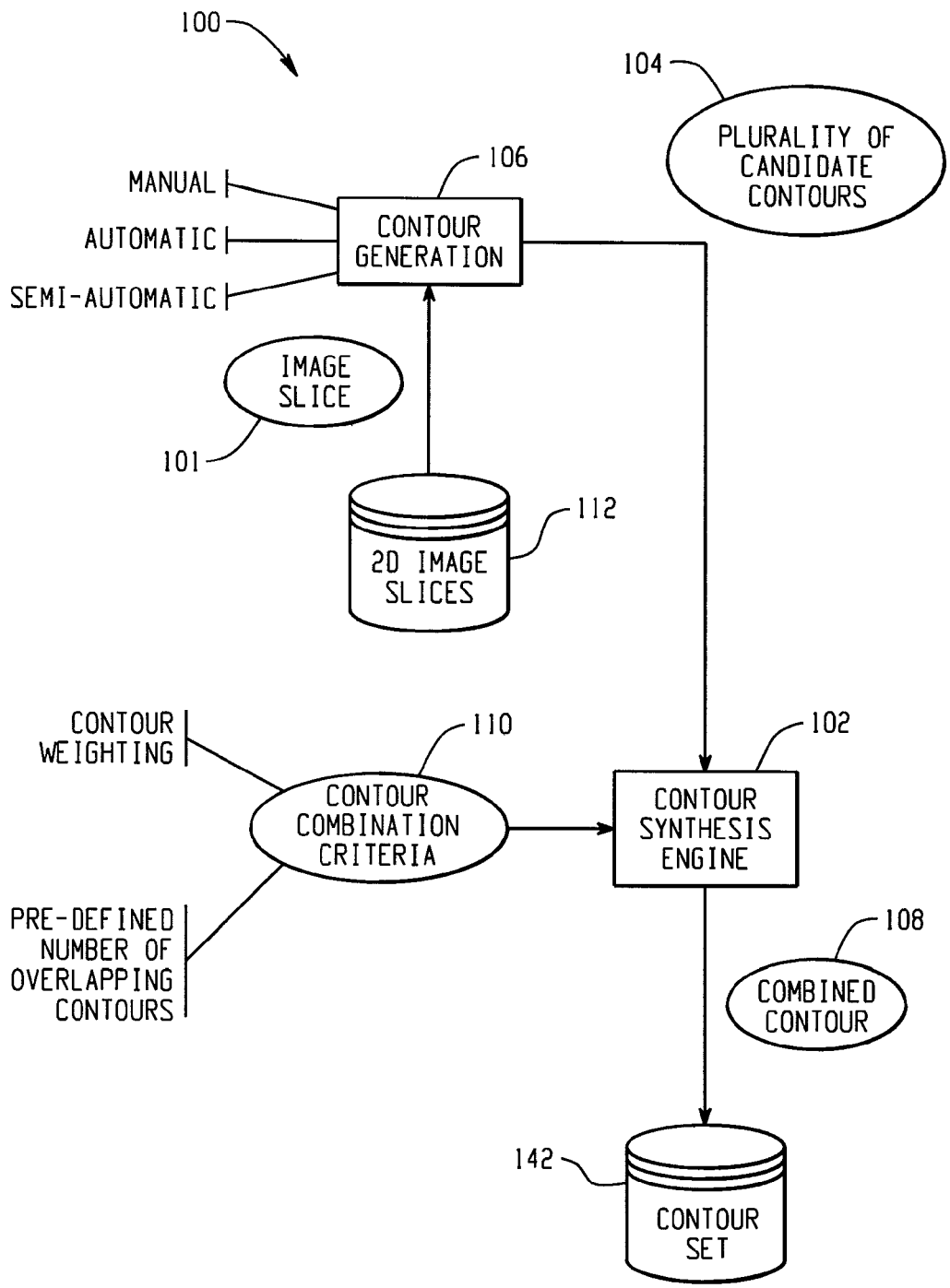
FIGS. 1, 3 and 6 are block diagrams of example systems for combining a plurality of candidate contours to generate a contour for a medical image.

FIG. 1 is a block diagram of an example system 100 for combining a plurality of candidate contours to generate a contour for a medical image. The system 100 includes a contour synthesis engine 102 that receives a plurality of candidate contours 104 for the medical image 101 from one or more contour generation mechanisms 106. The candidate contours 104 are each generated to identify the same one or more objects within the medical image 101. For instance, each of the candidate contours 104 may attempt to outline the same one or more pieces of anatomy within the image 101 with varying degrees of accuracy. In order to create a contour that more accurately identifies the one or more objects within the medical image 101, the contour synthesis engine 102 synthesizes a combined contour 108 from the plurality of candidate contours 104 by selecting portions of the plurality of candidate contours based on one or more pre-defined contour combination criterion 110.

The medical image 101 may be a two-dimensional (2D) image slice from a set of 2D images stored in an image database 112. The set of 2D images may, for example, be received in the image database 112 from a CT scanner or other system for capturing a three-dimensional (3D) medical image in the form of a set of 2D image slices. The medical image 101 is contoured using one or more of a variety of available contour mechanisms 106 to create the plurality of candidate contours 104. As illustrated, the contour mechanisms 106 used to create the candidate contours 104 may include manual, automatic, or semi-automatic contouring software. For example, the candidate contours 104 could include contours that were created using different types of available automatic or semi-automatic contouring software, such as atlas-based segmentation or model-based segmentation. In another example, the candidate contours 104 may include one or more contours that were created using manual contour software, for instance by an attending physician or technician.

Figure 8:
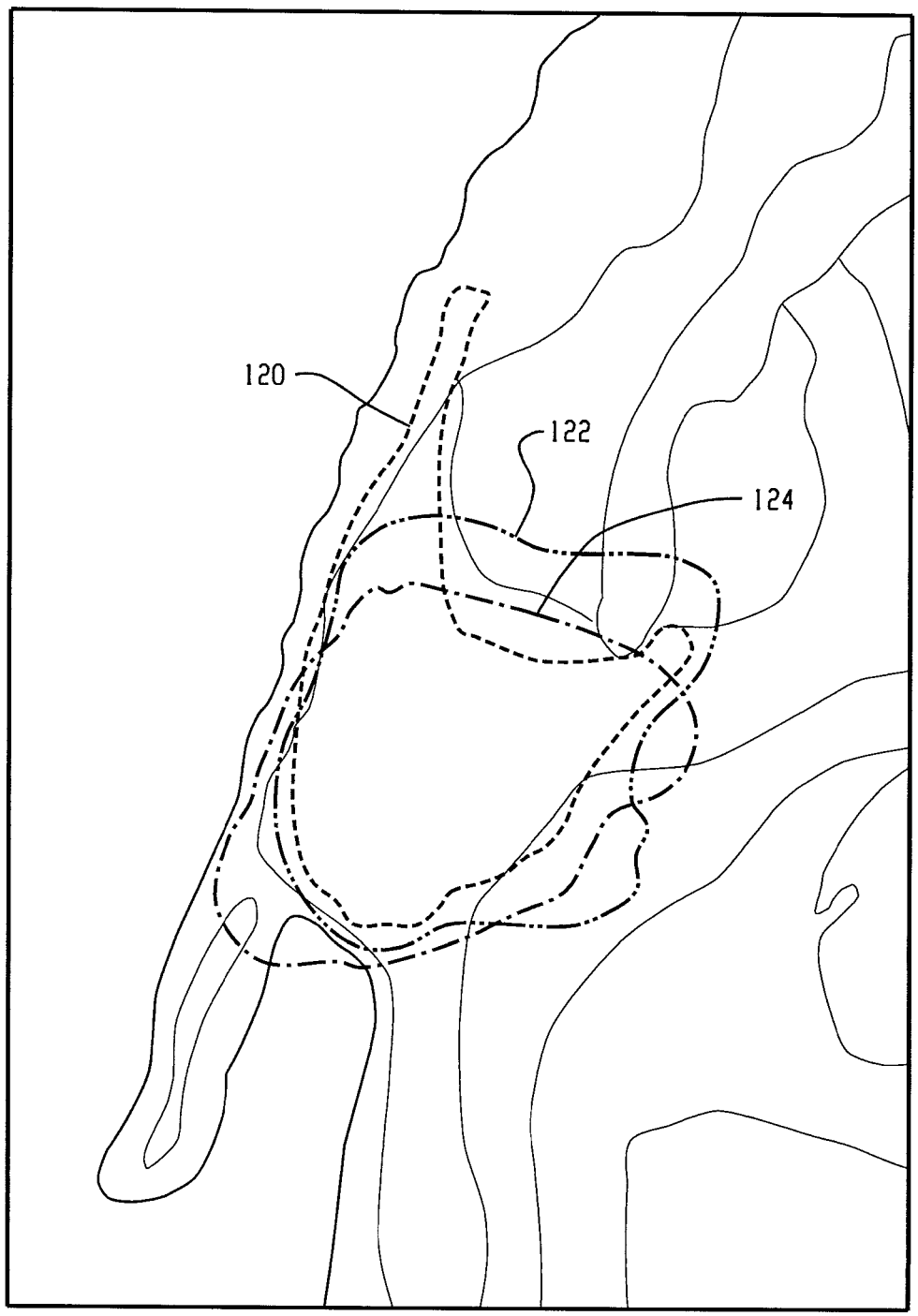
FIG. 8 is an example of a plurality of candidate contours.

An example image with three candidate contours is illustrated in FIG. 8. In this example, three separate candidate contours 120, 122, 124 have been generated to identify the same piece of anatomy within a 2D image slice. Specifically, each of the candidate contours 120, 122, 124 shown in FIG. 8 is attempting to outline a parotid gland within a 2D image slice from a CT scan of a patient's head and neck.

With reference again to FIG. 1, the contour synthesis engine 102 selects portions of the candidate contours 104 in order to synthesize a combined contour 108 based on one or more pre-defined contour combination criterion 110. In one embodiment, the pre-defined contour combination criteria 110 may include a pre-defined number of overlapping contours such that any portion of the candidate contours 104 that includes at least the pre-defined number of overlapping contours is included in the combined contour 108. For example, the contour combination criteria 110 may specify that the combined contour 108 include any contour region where two or more of the candidate contours 104 overlap, where a contour region is an area that is defined between the intersections of the edges of least two of the candidate contours 104. In another example, the pre-defined number of overlapping contours may be a variable that is dependent on the total number of candidate contours.

Figure 9:
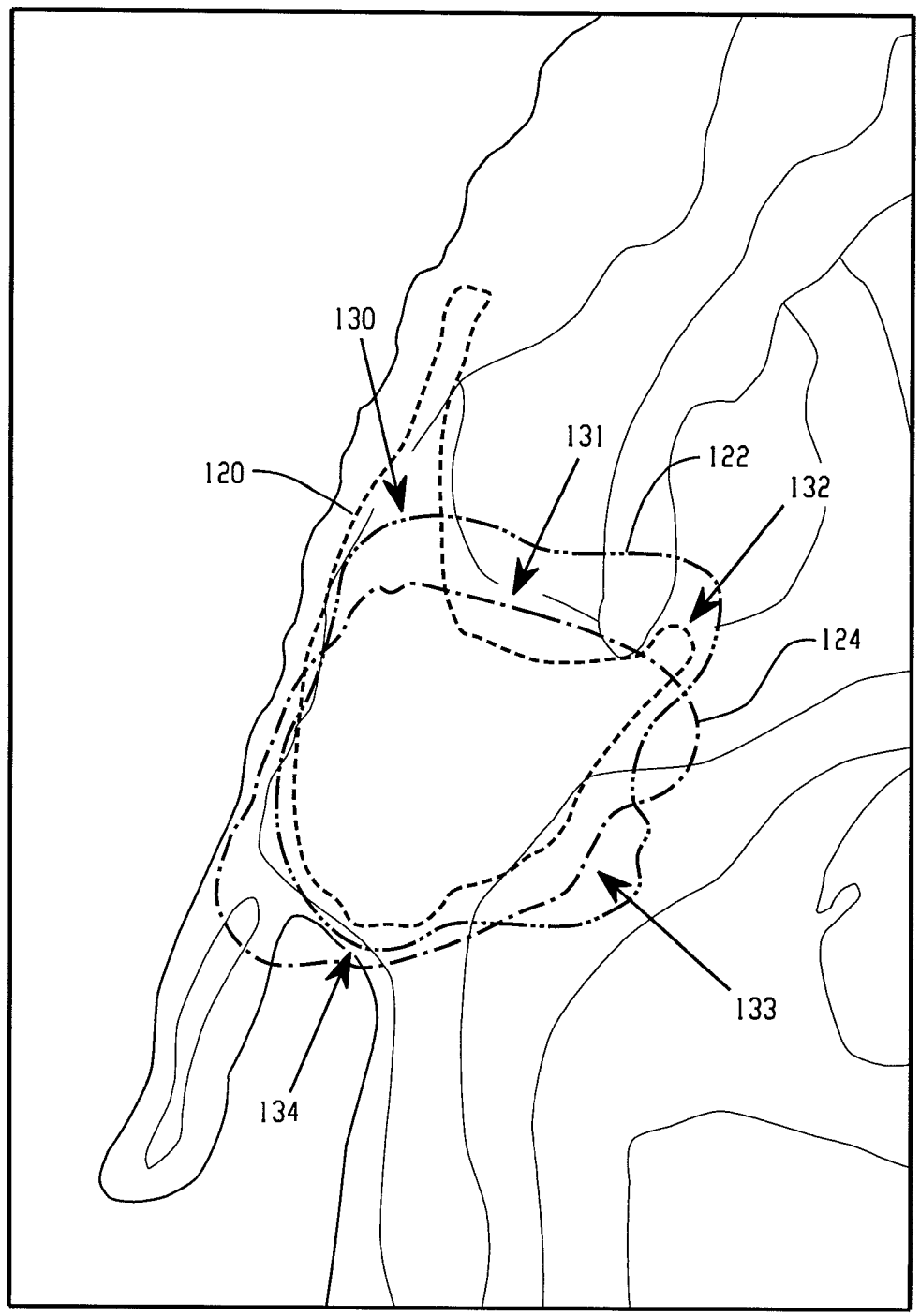
FIGS. 9 and 10 illustrate an example of a combined contour that is synthesized from a plurality of candidate contours.
Figure 10:
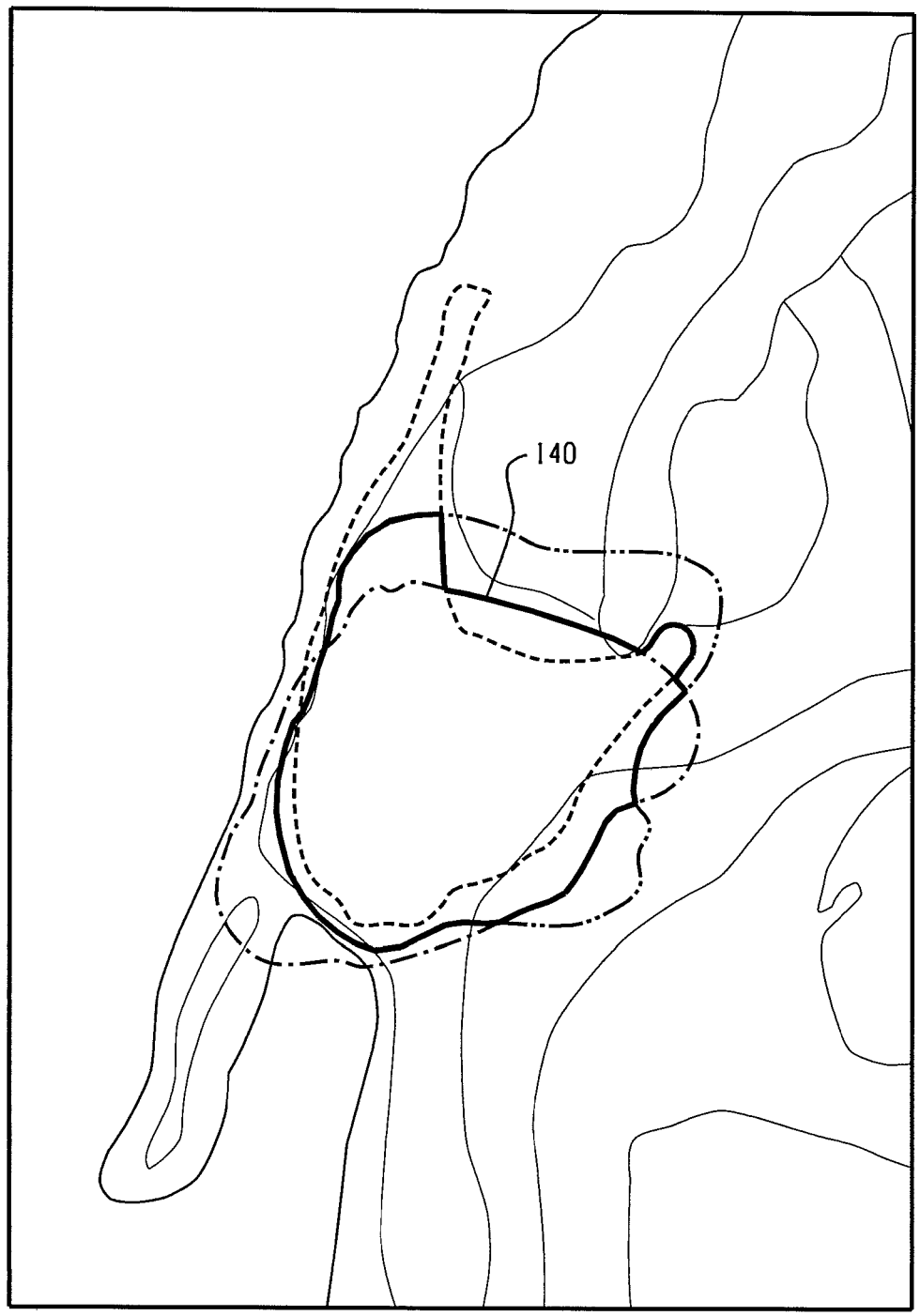

FIGS. 9 and 10 illustrate an example in which a combined contour is synthesized based on a contour combination criteria that specifies that the combined contour include any region where two or more of the candidate contours overlap. FIG. 9 shows the same three candidate contours 120, 122, 124 described above with reference to FIG. 8. In addition, FIG. 9 shows five arrows 130-134 that are included to illustrate the edges of the regions where two or more of the three candidate contours 120, 122, 124 overlap. Specifically, arrow 130 points to the edge of a region where contours 120 and 122 overlap, arrow 131 points to the edge of a region where contours 122 and 124 overlap, arrow 132 points to the edge of a region where contours 120 and 122 overlap, arrow 133 points to the edge of a region where contours 120 and 124 overlap, and arrow 134 points to the edge of a region where contours 120 and 122 overlap. As shown in FIG. 10, these regions with overlapping candidate contours are selected to synthesize a combined contour 140. The combined contour 140 is illustrated by a solid line in FIG. 10.

With reference again to FIG. 1, in another embodiment, the contour combination criteria 110 may include contour weighting criteria that gives one or more of the candidate contours 104 priority over the others. For example, one of the candidate contours 104 may be generated using a contour generation mechanism 106 that is deemed more accurate than the others and is therefore given a higher weight. The combined contour 108 may then be generated by adjusting the higher-weighted contour based on the lower-weighted contour(s). For instance, a higher-weighted contour may be expanded to include a region where a pre-defined number of lower-weighted contours overlap. In another example, the contour weighting may determine a number of contour overlaps required for inclusion in the combined contour. For example, in one embodiment a region from a heavier-weighed contour may be included in the combined contour if it overlaps with any one additional contour, where lower-weighted contours may be required to overlap with more than one additional contour (where the number of required overlapping contours depends on the weighting.)

FIG. 1 also illustrates a contour database 142 that stores the combined contour data 108 generated by the contour synthesis engine 102. When the system 100 of FIG. 1 is used to contour a set of 2D image slices 112 that make up a 3D medical image, the process described above may, for example, be repeated for each 2D image slice in the set, and the combined contour data 108 for each slice 101 may be stored in the contour database 142 to make up a 3D contour.

In one embodiment, a 3D representation of the contours in the contour database 142 may be viewable, for example as 3D mesh objects or 3D bitmasks. In addition, in certain examples, the candidate contour overlaps may be computed and combined using the 3D representation.

It should be understood that contour synthesis engine, along with other software components described herein, may be implemented by software instructions executing on one or more processing devices. In other implementations, however, one or more operations of these software components may instead be performed by other known mechanisms such as firmware or even appropriately designed hardware. The image database and contour database, as described herein, may be implemented using one or more memory devices. For instance, in one example the image database and contour database may be implemented within the same memory device, and in another example they may be implemented on separate memory devices.

Figure 2:
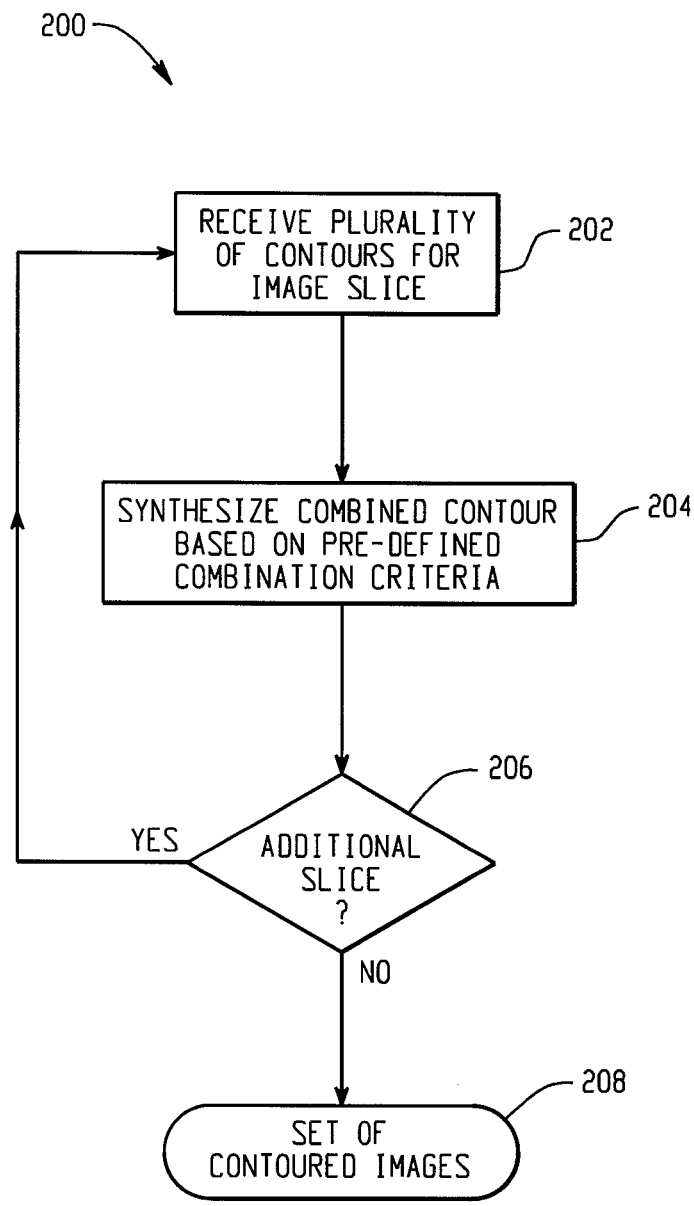
FIGS. 2, 4, 5 and 7 are flow diagrams of example methods for combining a plurality of candidate contours to generate a contour for a medical image.

FIG. 2 is a flow diagram of an example method 200 for combining a plurality of candidate contours to generate a contour for a medical image. In step 202, a plurality of contours are received for the medical image, where each of the contours where generated to identify the same one or more objects (e.g., pieces of anatomy) within the medical image. The medical image may, for example, be a two-dimensional (2D) image slice from a set of 2D images received from a CT scanner or other system for capturing a three-dimensional (3D) medical image in the form of a set of 2D image slices. The plurality of contours received in step 202 may have been generated, for example, using one or more of a variety of available contour mechanisms, such as manual, automatic, and/or semi-automatic contouring software.

At step 204, a combined contour is synthesized by selecting portions of the plurality of received contours based on one or more pre-defined combination criterion. For example, in one embodiment, the pre-defined combination criteria may include a pre-defined number of overlapping contours such that any portion of the received contours that includes at least the pre-defined number of overlapping contours is included in the combined contour. For example, the contour combination criteria may specify that the combined contour include any region where two or more of the received contours overlap. In another example, the pre-defined number of overlapping contours may be dependent on the total number of candidate contours.

In another embodiment, the contour combination criteria may include contour weighting criteria that gives one or more of the received contours priority over the others. For example, one of the received contours may be given a higher weight than the others, and the combined contour may then be generated by adjusting the higher-weighted contour based on the lower-weighted contour(s). For instance, a higher-weighted contour may be expanded to include a region where a pre-defined number of lower-weighted contours overlap. In another example, the contour weighting may determine a number of contour overlaps required for inclusion in the combined contour. For example, in one embodiment a region from a heavier-weighed contour may be included in the combined contour if it overlaps with any one additional contour, where lower-weighted contours may be required to overlap with more than one additional contour (where the number of required overlapping contours depends on the weighting.)

In decision step 206, the method 200 determines if there is an additional image slice to contour. For example, when the method 200 is used to contour a set of 2D image slices that make up a 3D medical image, the method may be repeated for each 2D image slice in the set. If one or more uncontoured images remain, then the method returns to step 202. Otherwise, when contouring is complete the method continues to step 208 where a set of contoured images has been generated. The set of contoured images may, for example, make up a 3D contour.

It should be understood that similar to the other processing flows described herein, one or more of the steps and the order in the flowchart may be altered, deleted, modified and/or augmented and still achieve the desired outcome.

Figure 3:
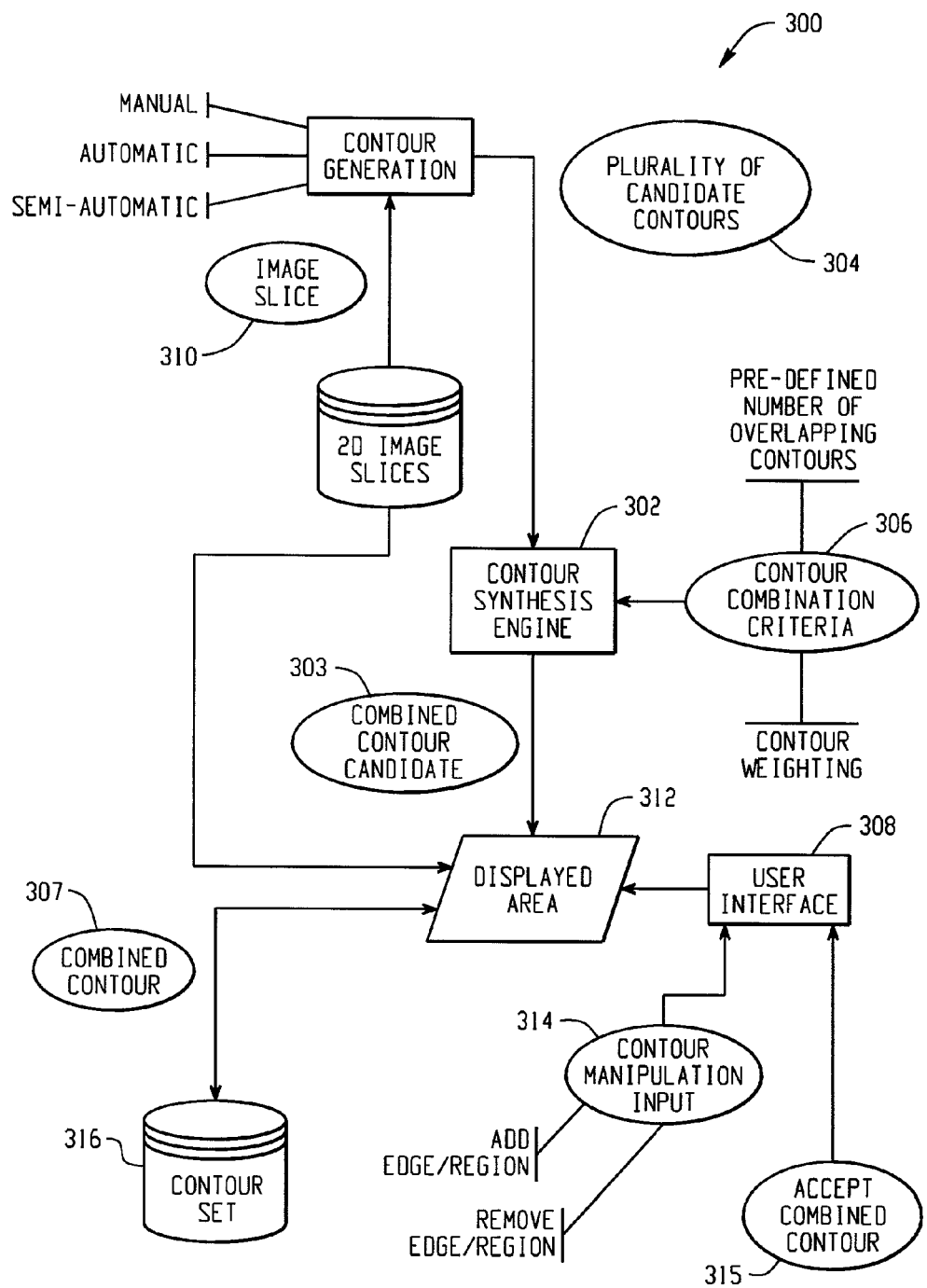

FIG. 3 is a block diagram of another example system 300 for combining a plurality of candidate contours to generate a contour for a medical image. The system includes a contour synthesis engine 302 that synthesizes a combined contour candidate 303 from a plurality of candidate contours 304 based on one or more pre-defined contour combination criterion 306, as described above with reference to FIG. 1. In addition, this example also includes a user interface 308 to enable a user to modify the combined contour candidate 303, if desired, to generate the final combined contour data 307.

In operation, the combined contour candidate 303 from the contour synthesis engine 302 is overlaid onto the medical image 310 on a display area 312 along with the plurality of candidate contours 304. The user interface 308 may receive contour manipulation input 314 to modify the combined contour candidate 303 displayed in the display area 312 in order to add or remove one or more regions from the plurality of candidate contours 304. In addition, the user interface 308 may also receive input 315 to accept the combined contour candidate 303 as the final combined contour 307 (with or without modifications).

For example, the user interface 308 may be a graphical user interface that is configured to receive user inputs 314, 315 via the displayed area 312 in order to add or remove a region from the combined contour candidate 303 (if desired) and to accept the combined contour candidate 303 as the final combined contour 307. In one example, the user interface 308 may enable the user to add a region to the combined contour candidate 303 by selecting a region of one of the candidate contours 304 that was not included in the combined contour candidate by the contour synthesis engine 302. Similarly, the user interface 308 may enable the user to select a region to remove from the combined contour candidate 303. A contour region may, for example, be an area that is defined between the intersections of the edges of least two of the candidate contours 304.

Figure 11:
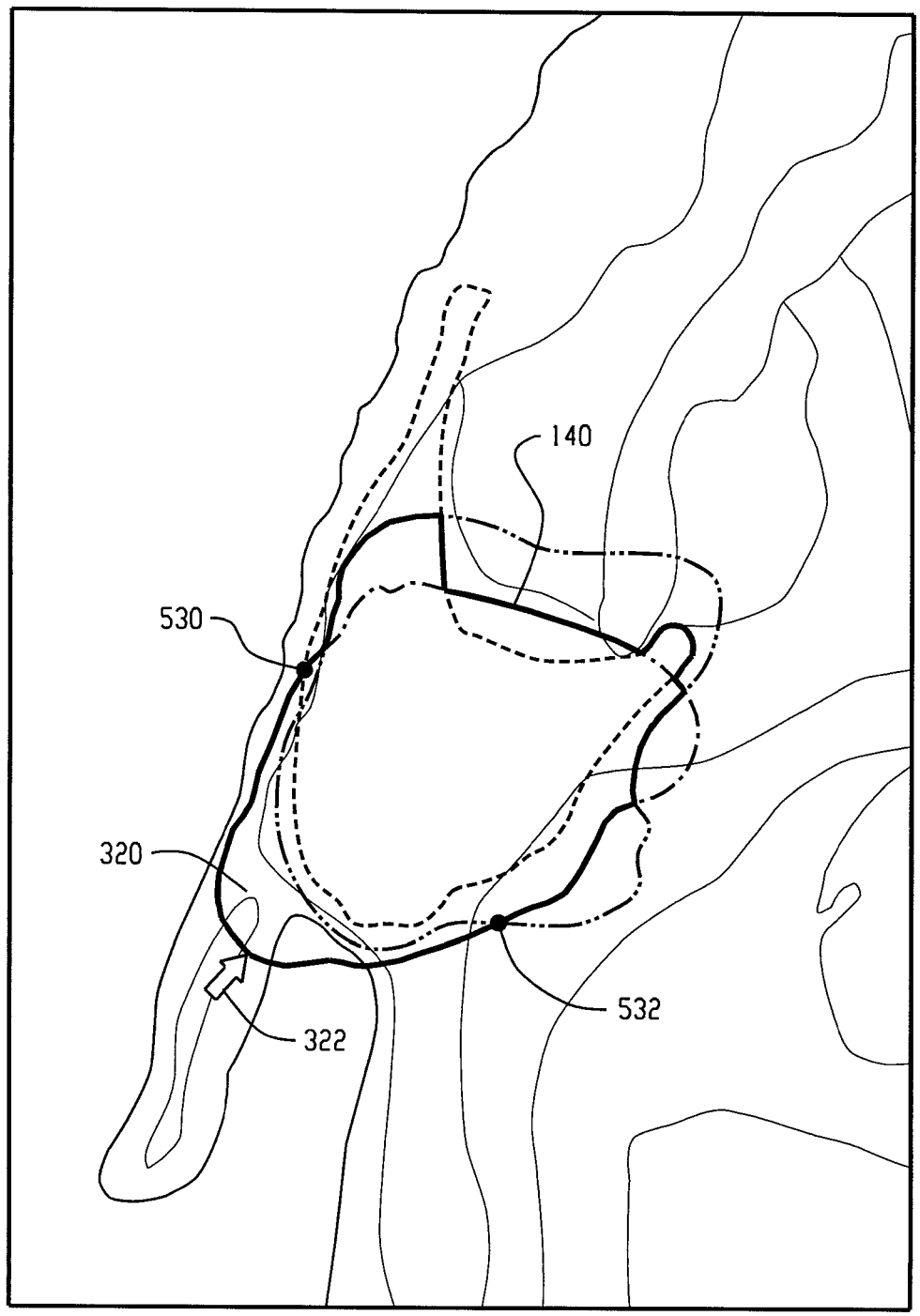
FIG. 11 illustrates an example of a user interface for modifying a combined contour.

An example of adding a region to a combined contour candidate is illustrated in FIGS. 10 and 11. In FIG. 10, the combined contour candidate 140 is displayed on the medical image along with the candidate contours. In FIG. 11, an additional region 320 has been added to the combined contour candidate 140 based on a user input. For example, the additional region 320 may have been added via a graphical user interface by the user positioning a cursor 322 within the region or on the edge of the region and selecting an input, such as a mouse button click. In one example, regions may be added to the combined contour candidate 140 by positioning a cursor 322 within a region outside of the combined contour candidate 140 and clicking a mouse button, and regions may be removed from the combined contour candidate 140 by positioning a cursor 322 within a region inside of the combined contour candidate 140 and clicking a mouse button.

With reference again to FIG. 3, once the combined contour candidate 303 has been accepted 315, it is stored as the combined contour 307 in the contour database 316. In one example, the combined contour 307 may also be displayed in the display area 312 by removing the plurality of candidate contours 304 from the display once the combined contour candidate 303 has been accepted.

When the system 300 of FIG. 3 is used to contour a set of 2D image slices that make up a 3D medical image, the process described above may, for example, be repeated for each 2D image slice in the set, and the combined contour data 307 for each slice 310 may be stored in the contour database 316 to make up a 3D contour.

In one embodiment, the user interface 308 may also be configured to receive an input to cause the 3D contour to be displayed in the display area 312. In certain examples, a 3D combined contour may be displayed along with one or more candidate contours (2D or 3D), and the user may be able to edit the 3D contour via the user interface 308 by adding or removing multi-slice regions from the 3D combined contour.

Figure 4:
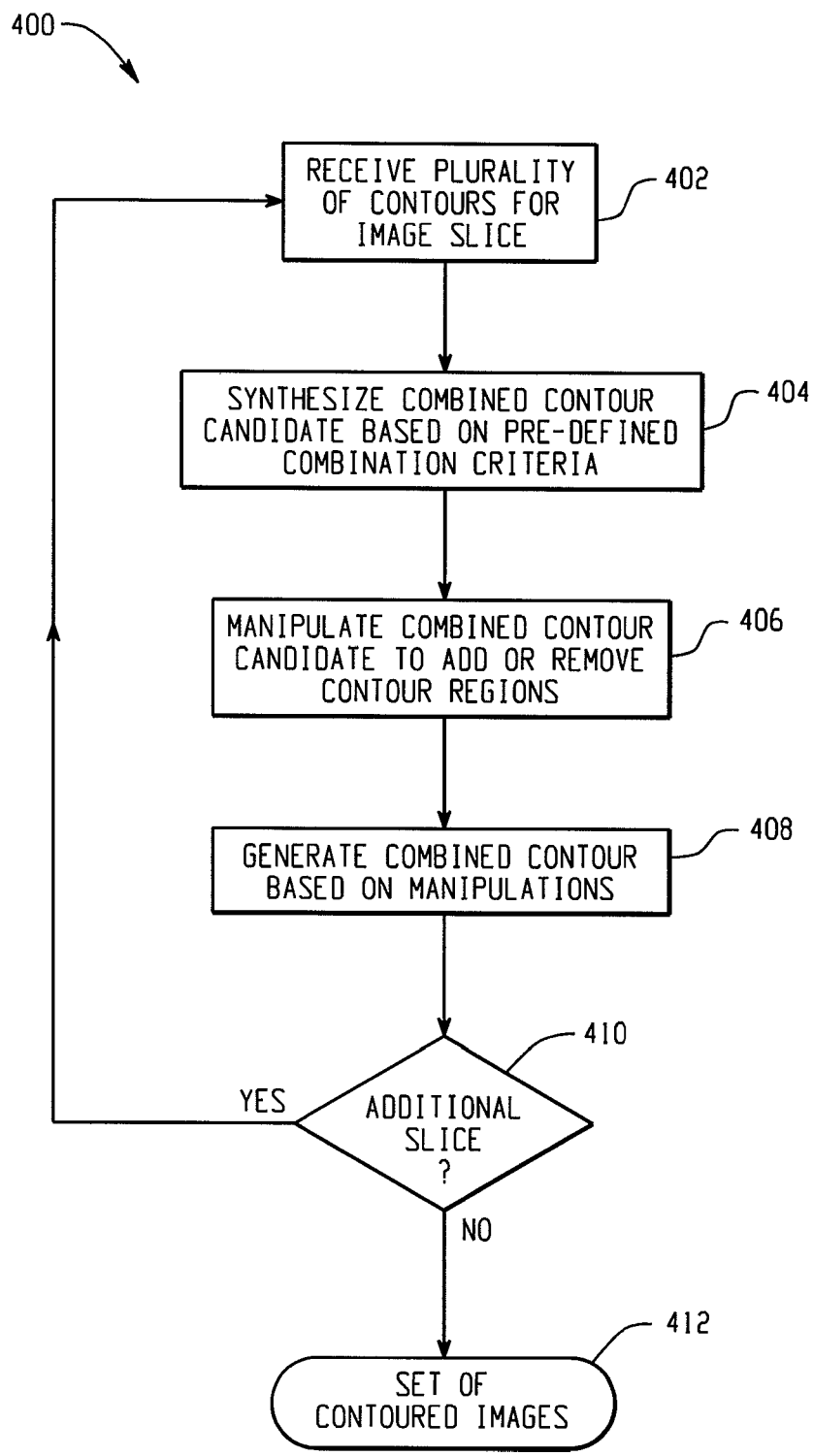

FIG. 4 is a flow diagram of another example method 400 for combining a plurality of candidate contours to generate a contour for a medical image. In step 402, a plurality of contours are received that identify one or more objects within a medical image. The medical image may, for example, be a two-dimensional (2D) image slice from a set of 2D images received from a CT scanner or other system for capturing a three-dimensional (3D) medical image in the form of a set of 2D image slices. The plurality of contours received in step 402 may have been generated, for example, using one or more of a variety of available contour mechanisms, such as manual, automatic, and/or semi-automatic contouring software.

At step 404, a combined contour candidate is synthesized by selecting portions of the plurality of received contours based on one or more pre-defined combination criterion. For example, in one embodiment, the pre-defined combination criteria may include a pre-defined number of overlapping contours such that any portion of the received contours that includes at least the pre-defined number of overlapping contours is included in the combined contour candidate. In another embodiment, the contour combination criteria may include contour weighting criteria that gives one or more of the of the received contours priority over the others.

At step 406, the combined contour candidate may be manipulated (if desired) to add or remove one or more contour regions. In one example, graphical user interface may be used to add a region to the combined contour candidate by selecting a region of one of the candidate contours that was not included in the combined contour candidate. Similarly, a graphical user interface may be used to select a region to remove from the combined contour candidate. A contour region may, for example, be an area that is defined between the intersections of the edges of least two of the candidate contours.

At step 408, the final combined contour for the image is create that includes any manipulations to the combined contour candidate that were received in step 406. For example, the final combined contour may be generated when a user input is received indicating that the combined contour candidate (including any manipulations) is acceptable.

In decision step 410, the method 400 determines if there is an additional image slice to contour. For example, when the method 400 is used to contour a set of 2D image slices that make up a 3D medical image, the method may be repeated for each 2D image slice in the set. If one or more uncontoured images remain, then the method returns to step 402. Otherwise, when contouring is complete the method continues to step 412 where a set of contoured images has been generated. The set of contoured images may, for example, make up a 3D contour.

Figure 5:
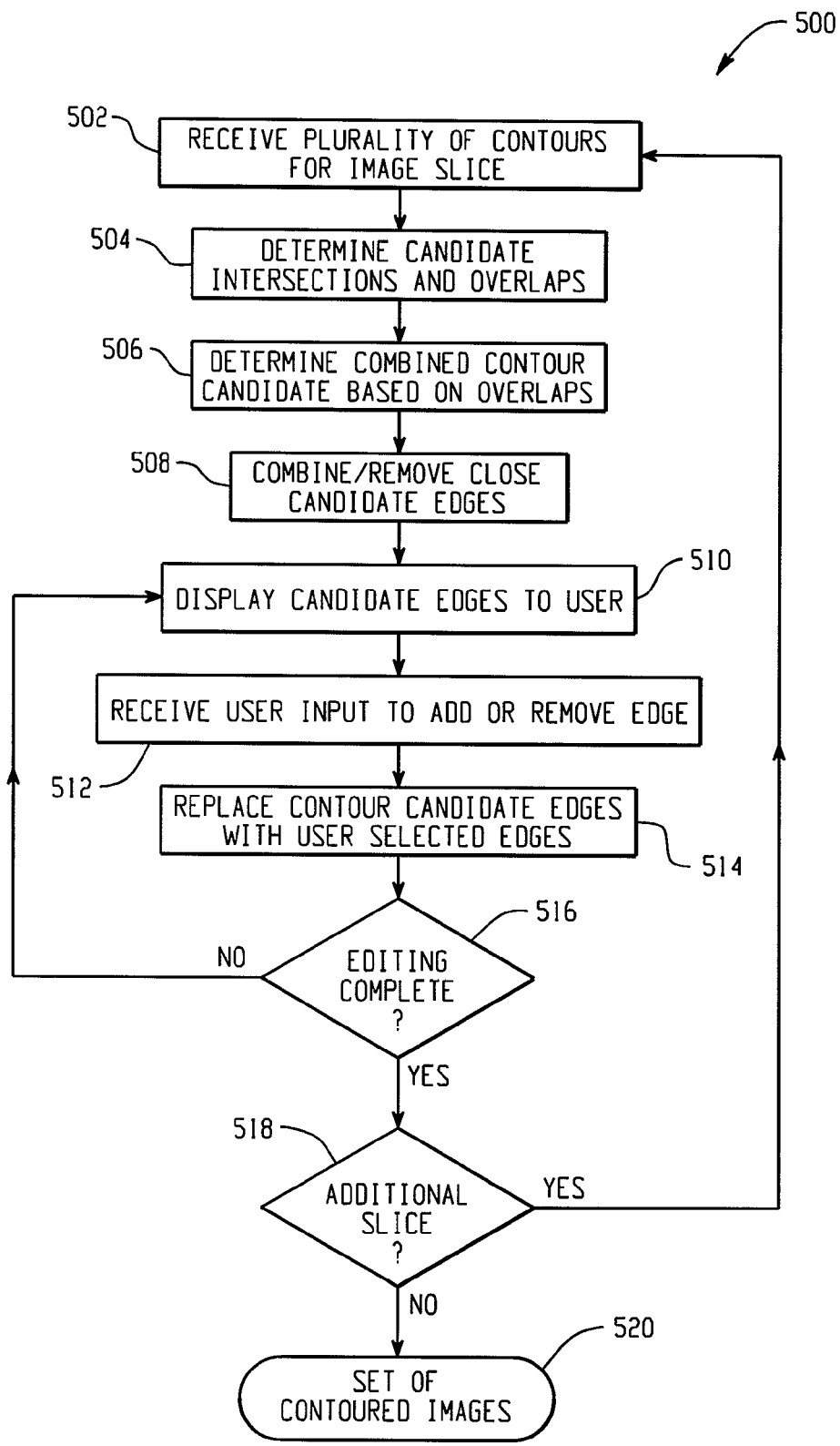

FIG. 5 is a flow diagram of an additional example method 500 for combining a plurality of candidate contours to generate a contour for a medical image. In step 502, a plurality of candidate contours are received that identify one or more objects within the medical image. The medical image may, for example, be a two-dimensional (2D) image slice from a set of 2D images received from a CT scanner or other system for capturing a three-dimensional (3D) medical image in the form of a set of 2D image slices. The plurality of contours received in step 502 may have been generated, for example, using one or more of a variety of available contour mechanisms, such as manual, automatic, and/or semi-automatic contouring software.

At step 504, the plurality of candidate contours are analyzed to identify contour intersections and to identify overlapping contours. Contour intersections are identified to identify regions that may be included in the combined contour. A contour region may include the area that is defined between at least two contour intersections. For example, in FIG. 11 contour region 320 includes the area bounded by the edges of two candidate contours between the contour intersections labeled 530 and 532. Overlapping contours are identified in order to identify contour regions to be included within a combined contour.

At step 506, a combined contour candidate is synthesized by selecting regions of the plurality of received contours based on the number of overlapping contours in the region. For example, the combined contour candidate may include any region where two or more of the candidate contours overlap. In another example, the number of overlapping contours required for a region to be included in the combined contour candidate may be dependent on the total number of candidate contours.

At step 510, the edges of the combined candidate contour (i.e., the contour outline) may be displayed on the medical image along with the edges of the plurality of candidate contours (e.g., as shown in FIG. 10). In addition, prior to display at step 508, any edges of the plurality of candidate contours that are very close (i.e., within a predefined distance) to one another may be combined into a single edge or one of the edges removed. In this way, unnecessary (i.e., overly small) contour regions will be removed from the display and the displayed contours will not appear overly cluttered to the user.

At step 512, the combined contour candidate may be manipulated (if desired) to add or remove a contour region. If any manipulations are made, then an edge from the combined contour candidate is replaced with the edge from the selected contour region in step 514 (see, e.g., FIG. 11). In one example, a graphical user interface may be used to add a region to the combined contour candidate by selecting a region (or region edge) of one of the candidate contours that was not included in the combined contour candidate. Similarly, a graphical user interface may be used to select a region (or region edge) to remove from the combined contour candidate. At decision step 516, the method determines if the contour editing is complete. For example, the editing may be completed by receiving a user input to accept the combined contour candidate as the final combined contour. If editing is not complete, then the method returns to step 510. Otherwise, when editing is complete the method proceeds to step 518.

In decision step 518, the method 500 determines if there is an additional image slice to contour. For example, when the method 500 is used to contour a set of 2D image slices that make up a 3D medical image, the method may be repeated for each 2D image slice in the set. If one or more uncontoured images remain, then the method returns to step 502. Otherwise, when contouring is complete the method continues to step 520 where a set of contoured images has been generated. The set of contoured images may, for example, make up a 3D contour.

Figure 6:
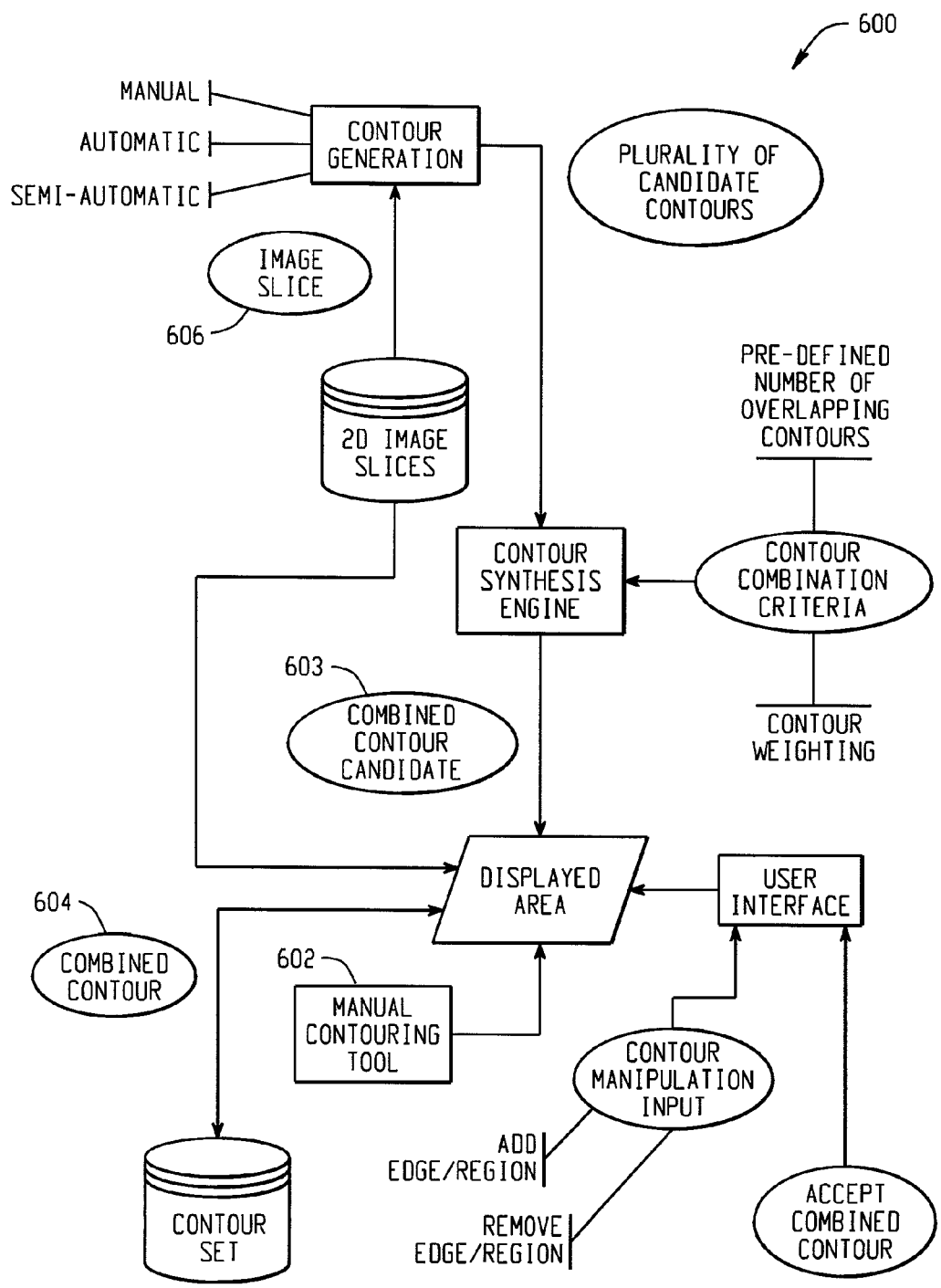

FIG. 6 is a block diagram of yet another example system 600 for combining a plurality of candidate contours to generate a contour for a medical image. This example is similar to the system described above with reference to FIG. 3, except that it also includes a manual contouring tool 602. The manual contouring tool 602 may be used to make additional edits to the combined contour candidate 603 before it is accepted as the final combined contour 604 for the image slice 606.

Figure 7:
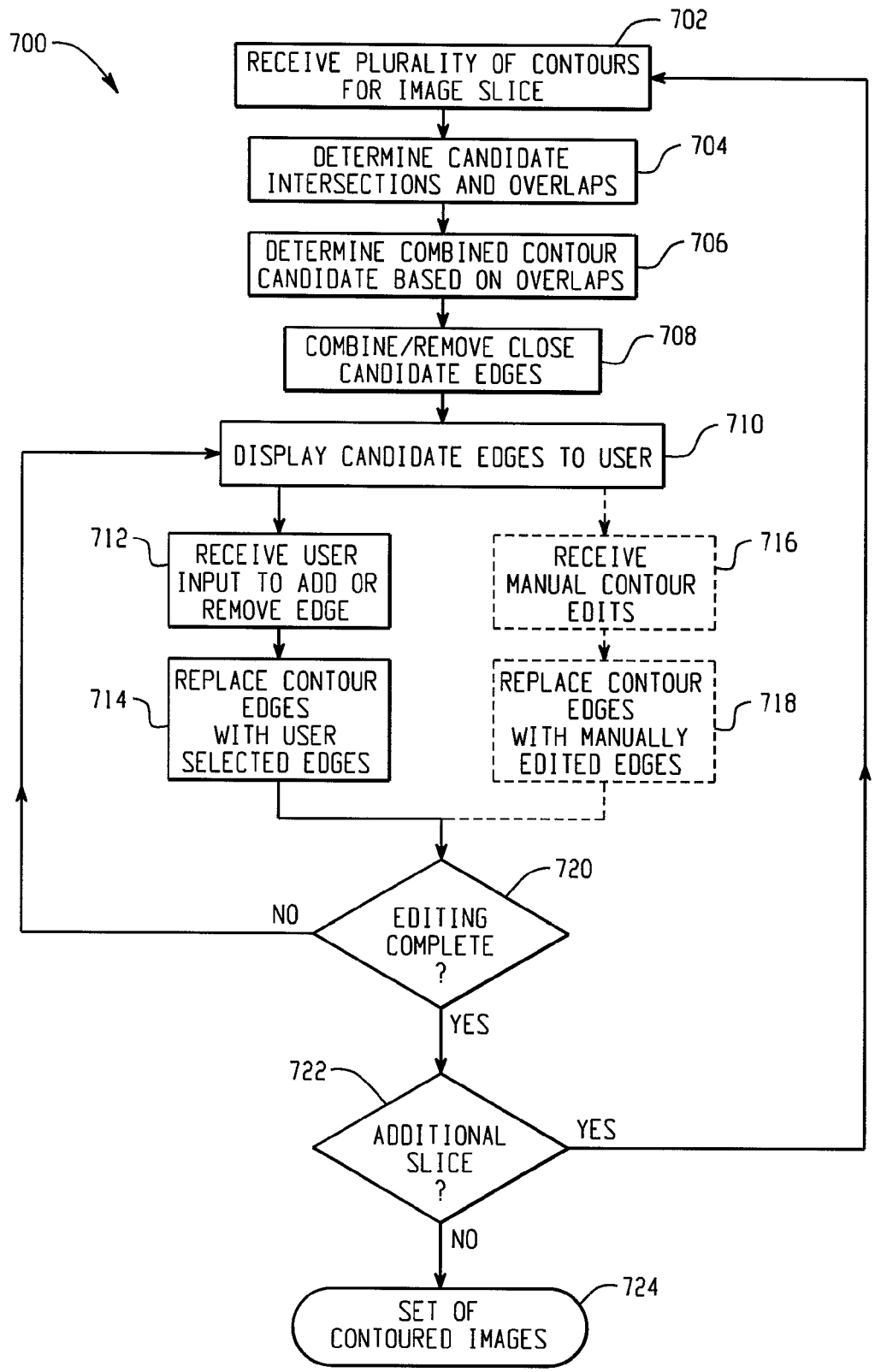

FIG. 7 is a flow diagram of yet another example method 700 for combining a plurality of candidate contours to generate a contour for a medical image. In step 702, a plurality of candidate contours are received that identify one or more objects within the medical image. At step 704, the plurality of candidate contours are analyzed to identify contour intersections and to identify overlapping contours, as described above with reference to FIG. 5. Then, at step 706, a combined contour candidate is synthesized by selecting regions of the plurality of received contours based on the number of overlapping contours in the region.

At step 710, the edges of the combined candidate contour (i.e., the contour outline) may be displayed on the medical image along with the edges of the plurality of candidate contours (e.g., as shown in FIG. 10). In addition, prior to display at step 708, any edges of the plurality of candidate contours that are very close (i.e., within a predefined distance) to one another may be combined into a single edge or one of the edges removed.

After step 710, the user may proceed either to step 712 to add or remove contour regions or to step 716 to edit the combined candidate contour using manual contouring software. This option is indicated in the drawing by including steps 716 and 718 within dotted boxes. It should also be understood that the user may also choose not the edit the candidate contour in any way, thus skipping all of steps 712, 714, 716 and 718.

At step 712, the combined contour candidate may be manipulated (if desired) to add or remove a contour region. If any manipulations are made, then an edge from the combined contour candidate is replaced with the edge from the selected contour region in step 714 (see, e.g., FIG. 11). At step 716, the combined contour candidate may be manually edited (if desired) using manual contouring software. If any manual edits are made, then the edited edge(s) of the combined contour candidate are replaced with the edited edge(s) at step 718.

At decision step 720, the method determines if the contour editing is complete. For example, the editing may be completed by receiving a user input to accept the combined contour candidate as the final combined contour. If editing is not complete, then the method returns to step 710. Otherwise, when editing is complete the method proceeds to step 722.

At decision step 722, the method 700 determines if there is an additional image slice to contour. For example, when the method 700 is used to contour a set of 2D image slices that make up a 3D medical image, the method may be repeated for each 2D image slice in the set. If one or more uncontoured images remain, then the method returns to step 702. Otherwise, when contouring is complete the method continues to step 724 where a set of contoured images has been generated. The set of contoured images may, for example, make up a 3D contour.

Figure 12:
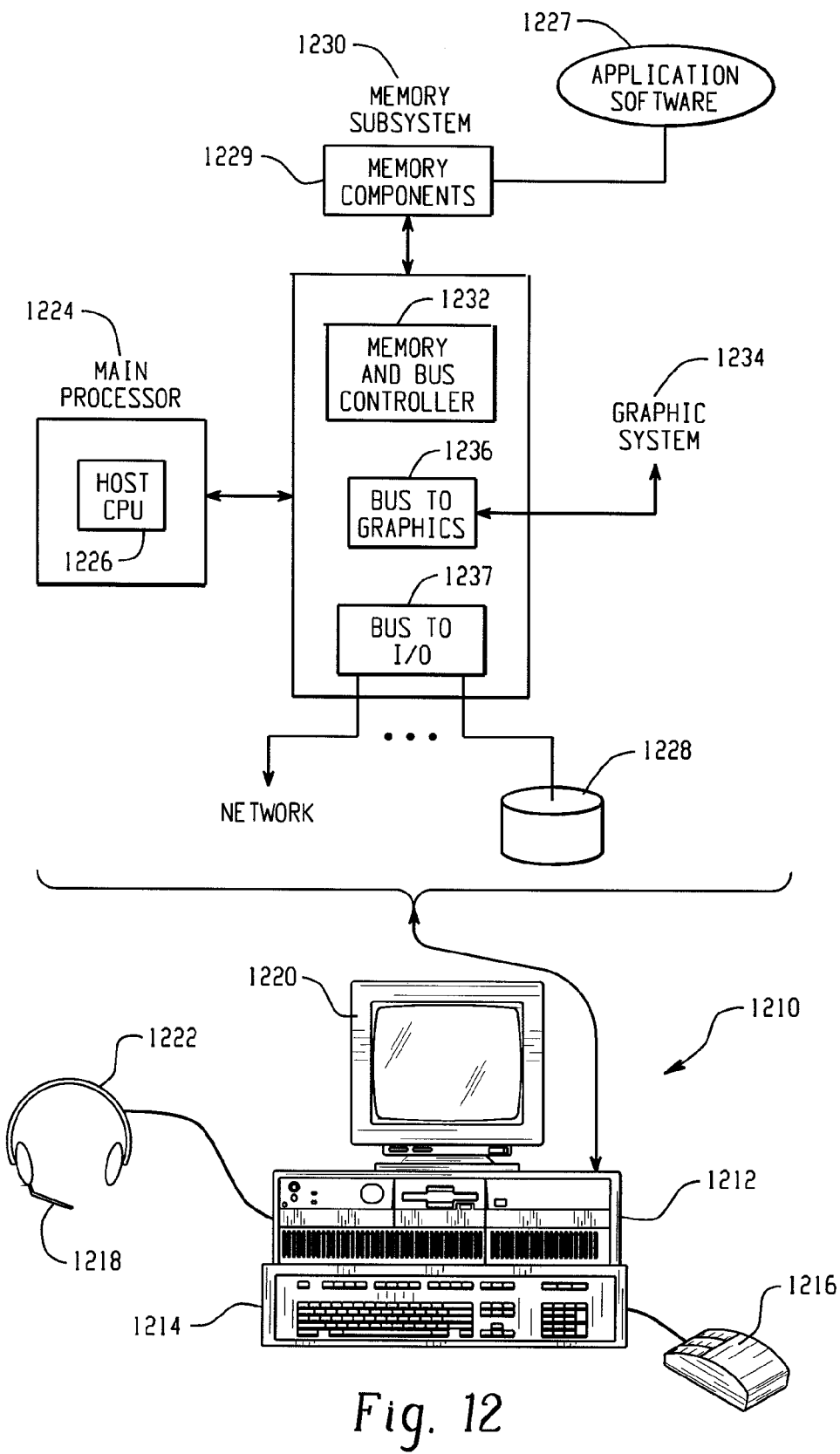
FIG. 12 is a block diagram of hardware which may be used to implement the various embodiments described herein.

FIG. 12 is a block diagram of hardware 1210 which may be used to implement the various embodiments of the method of the present invention. The hardware 1210 may be a personal computer system or server system that includes a computer having as input devices keyboard 1214, mouse 1216, and microphone 1218. Output devices such as a monitor 1220 and speakers 1222 may also be provided. The reader will recognize that other types of input and output devices may be provided and that the present invention is not limited by the particular hardware configuration.

Residing within computer 1220 is a main processor 1224 which is comprised of a host central processing unit 1226 (CPU). Software applications 1227 may be loaded from, for example, disk 1228 (or other device), into main memory 1229 from which the software application 1227 may be run on the host CPU 1226. The main processor 1224 operates in conjunction with a memory subsystem 1230. The memory subsystem 1230 is comprised of the main memory 1229, which may be comprised of a number of memory components, and a memory and bus controller 1232 which operates to control access to the main memory 1229. The main memory 1229 and controller 1232 may be in communication with a graphics system 1234 through a bus 1236. Other buses may exist, such as a PCI bus 1237, which interfaces to I/O devices or storage devices, such as disk 1228 or a CDROM, or to provide network access.

This written description uses examples to disclose the invention, including the best mode, and also to enable a person skilled in the art to make and use the invention. The patentable scope of the invention may include other examples that occur to those skilled in the art.

It is further noted that the systems and methods described herein may be implemented on various types of computer architectures, such as for example on a single general purpose computer or workstation, or on a networked system, or in a client-server configuration, or in an application service provider configuration.

Additionally, the methods and systems described herein may be implemented on many different types of processing devices by program code comprising program instructions that are executable by the device processing subsystem. In addition, the methods and systems may be implemented using one or more processors. The software program instructions may include source code, object code, machine code, or any other stored data that is operable to cause a processing system to perform methods described herein. Other implementations may also be used, however, such as firmware or even appropriately designed hardware configured to carry out the methods and systems described herein.

The systems' and methods' data (e.g., associations, mappings, etc.) may be stored and implemented in one or more different types of computer-implemented ways, such as different types of storage devices and programming constructs (e.g., data stores, RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It is claimed:

1. A system for generating a contour for a medical image, comprising:
   a contour synthesis engine configured to receive a plurality of contours for a medical image, the plurality of contours identifying at least one object within the medical image; the contour synthesis engine further configured to synthesize a combined contour from the plurality of contours by selecting portions of the plurality of contours based on one or more pre-defined contour combination criterion, the one or more pre-defined contour combination criterion including a designated number of contour overlaps such that any region where at least the designated number of contours are overlapping is included in the combined contour;
   wherein the contour synthesis engine comprises software instructions that are stored on one or more non-transitory, computer readable media and are executable by one or more processors.

2. The system of claim 1, wherein the designated number is two.

3. The system of claim 1, wherein the designated number is variable based on the number of contours included in the plurality of contours.

4. The system of claim 1, wherein the one or more pre-defined contour combination criterion includes contour weights that prioritizes at least one of the plurality of contours over at least another one of the plurality of contours.

5. The system of claim 4, wherein the designated number of contour overlaps is used to modify a highest-weighted one of the plurality of contours by adding regions from other ones of the plurality of contours.

6. The system of claim 1, wherein the plurality of contours are generated using different contour generation methods.

7. The system of claim 1, further comprising:
   a graphical user interface configured to display an overlay of the plurality of contours and the combined contour on the medical image.

8. The system of claim 7, wherein the graphical user interface is further configured to receive user input to modify the combined contour by adding an additional region from the plurality of contours.

9. The system of claim 8, wherein the additional region is defined by at least two edge intersections in the plurality of contours.

10. The system of claim 7, wherein the graphical user interface is further configured to receive user input to modify the combined contour by removing a region from the combined contour.

11. The system of claim 10, wherein the region to be removed is defined by at least two edge intersections in the plurality of contours.

12. The system of claim 7, wherein the graphical user interface is further configured to receive input from a manual contouring tool to modify the combined contour.

13. A processor-implemented method of generating a contour for a medical image, comprising:
   receiving a plurality of contours that identify an object within the medical image; and
   synthesizing a combined contour from the plurality of contours by selecting portions of the plurality of contours based on one or more pre-defined contour combination criterion;
   wherein the method is implemented using one or more processors executing software instructions stored on one or more non-transitory, computer readable media.

14. The method of claim 13, wherein the one or more pre-defined contour combination criterion comprises a pre-defined number of overlapping contours such that any portion of the plurality of contours that includes at least the pre-defined number of overlapping contours is included in the combined contour.

15. The method of claim 14, wherein the pre-defined number of overlapping contours is two.

16. The method of claim 13, wherein the one or more pre-defined contour combination criterion comprises a variable number of overlapping contours such that any portion of the plurality of contours that includes at least the variable number of overlapping contours is included in the combined contour, and wherein the variable number is dependent on the number of contours included in the plurality of contours.

17. The method of claim 13, wherein the one or more pre-defined contour combination criterion comprises contour weights that prioritizes at least one of the plurality of contours over at least another one of the plurality of contours.

18. The method of claim 13, wherein the plurality of contours are generated using different contour generation methods.

19. The method of claim 13, wherein the method is repeated for each of a plurality of medical image slices that together form a three dimensional medical image.

20. The method of claim 13, further comprising:
displaying an overlay of the plurality of contours and the combined contour on the medical image.

21. The method of claim 20, further comprising:
receiving a user input to modify the combined contour by adding an additional region from the plurality of contours.

22. The method of claim 21, wherein the additional region is defined by at least two edge intersections in the plurality of contours.

23. The method of claim 20, further comprising:
receiving a user input to modify the combined contour by removing a region from the combined contour.

24. The method of claim 23, wherein the region removed is defined by at least two edge intersections in the plurality of contours.

25. The method of claim 20, further comprising:
receiving an input from a manual contouring tool to modify the combined contour.

* * * * *